(12) United States Patent
Beckett et al.

(10) Patent No.: US 12,016,340 B2
(45) Date of Patent: Jun. 25, 2024

(54) SYNERGISTIC ANTIMICROBIAL FORMULATION CONSISTING OF PLANT EXTRACT AND LAURIC ARGINATE

(71) Applicant: KALAMAZOO HOLDINGS, INC., Kalamazoo, MI (US)

(72) Inventors: Amber Beckett, Kalamazoo, MI (US); Andrew Lee, Portage, MI (US); Roger Nahas, Portage, MI (US)

(73) Assignee: KALAMAZOO HOLDINGS, INC., Kalamazoo, MI (US)

( * ) Notice: Subject to any disclaimer, the term of this patent is extended or adjusted under 35 U.S.C. 154(b) by 31 days.

(21) Appl. No.: 17/065,963

(22) Filed: Oct. 8, 2020

(65) Prior Publication Data

US 2021/0106014 A1   Apr. 15, 2021

Related U.S. Application Data

(60) Provisional application No. 62/912,677, filed on Oct. 9, 2019.

(51) Int. Cl.
*A01N 65/22* (2009.01)
*A01N 37/44* (2006.01)

(52) U.S. Cl.
CPC .............. *A01N 65/22* (2013.01); *A01N 37/44* (2013.01)

(58) Field of Classification Search
CPC ................................. A01N 25/04; A01N 65/22
See application file for complete search history.

(56) References Cited

U.S. PATENT DOCUMENTS 10,624,368 B1 * 4/2020 Sawyer ................... A23B 4/20

FOREIGN PATENT DOCUMENTS

WO   WO-2013103556 A1 *  7/2013 ............. A01N 31/04

OTHER PUBLICATIONS

Ma et al., Food Chemistry, 206, 2016, 167-173.*
Ma et al., Int J Food Microbiology, 166, 2013, 77-84.*
Bitar, et al. J Am Oil Chem Soc, 85:641-646, 2008.
Chang, et al. Food Chemistry 172:298-304, 2015.
Chassaing, et al. Nature, 519:92-96, 2015.
Dai, et al. Journal of Food Protection 73:515-523, 2010.
Holder, et al. Scientific Reports, 9,172, pp. 1-14, published Jan. 17, 2019.
Kalemba and Kunicka, Current Medicinal Chemistry, 10:813-829, 2003.
Ma, Qiumin "Improving antimicrobial activity of lauric arginate by combination with essential oils for novel appliations." PhD dissertation, University of Tennessee, 2015.
Nair, et al. Poultry Science 93:2636-2640, 2014.
Oladunjoye, et al. Poultry Science 92:1357-1365, 2013.
Pei, et al. Journal of Food Science, vol. 74(4), pp. M379-M383, 2009.
Singh and Ishikawa, SOJ Microbiol Infect Dis. 4(1):1-18, 2016.
Singh, et al. Journal of Food Science, vol. 70(2), pp. M141-M148, published Feb. 15, 2005.
Soni, et al. International Journal of Food Microbiology, 155:82-88, 2012.
Ma, et al. International Journal of Food Microbiology, 166:77-84, 2013.

* cited by examiner

*Primary Examiner* — Kyle A Purdy
(74) *Attorney, Agent, or Firm* — HUESCHEN AND SAGE

(57) ABSTRACT

The present invention relates to novel synergistic compositions comprising known "clean-label" antimicrobial substances as well as processes for stabilizing food substances against typical food borne spoilage microorganisms and/or pathogens. It is a further object of the invention to provide novel combinations of "clean-label" antimicrobials which may be employed in such a process.

8 Claims, 4 Drawing Sheets

SYNERGISTIC ANTIMICROBIAL FORMULATION CONSISTING OF PLANT EXTRACT AND LAURIC ARGINATE

FIELD OF THE INVENTION

The present invention relates to antimicrobial processes and to novel antimicrobial compositions which may be employed in such processes. In search of a novel and powerful "clean-label" antimicrobial solution, lauric arginate based delivery systems for essential oil or plant extract-based antimicrobials were tested for synergistic antimicrobial effects. Surprising synergies were observed between thyme essential oil and lauric arginate in a markedly reduced concentration compared to previous formulations. Additionally, current formulations incorporated polysorbate 80 and an Ostwalt ripening inhibitor into the emulsion, however with the instant invention those components were successfully eliminated without sacrificing antimicrobial efficacy. Based on temporal analysis of lauric arginate treated *Zygosaccharomyces bailii*, the lauric arginate appears to potentiate antimicrobial efficacy, which could allow for end-use as a processing aid.

BACKGROUND OF THE INVENTION

Chemical preservatives in combination with various processing aids have been traditionally applied to food systems to prevent food spoilage microorganisms or foodborne pathogens. However, an increasing demand toward natural and additive-free food products from consumers prompted the food industry to seek effective "clean label" antimicrobial solutions which maintain safety and stability of the food products.

Many antimicrobials currently used in the food industry suffer from negative consumer perceptions as a result of names and routes of synthesis that sound non-"natural". The recitation of these antimicrobial agents on a food label can diminish sales and damage brand equity as consumers increasingly demand less processed/artificial and more "clean label" foods and food ingredients. Essential oils are an attractive target for formulating into antimicrobial agents due to their favorable perception by consumers, and "natural" sourcing.

Essential oils are mixture of volatile compounds extracted from plant biomass and have been identified as natural antimicrobial agents where the activity is mainly understood to arise from phenolic components. Essential oils (and other plant extracts) are commonly reported to have antimicrobial activity, and a large body of literature exists to support these claims. (Du, W. X. et al. Antibacterial effects of allspice, garlic, and oregano essential oils in tomato films determined by overlay and vapor-phase methods. *J. Food Sci.* 74:390-397 (2009). Pei, R. S., Zhou, F., Ji, B. P. & Xu, J. Evaluation of combined antibacterial effects of eugenol, cinnamaldehyde, thymol, and carvacrol against *E. coli* with an improved method. *J. Food Sci.* 74:379-383 (2009). Kalemba, D. & Kunicka, A. Antibacterial and antifungal properties of essential oils. *Curr Med Chem* 10:813-829 (2003). Singh, G., Marimuthu, P., De Heluani, C. S. & Catalan, C. Antimicrobial and antioxidant potentials of essential oil and acetone extract of *Myristica fragrans* Houtt. (aril part). *J. Food Sci.* Vol. 70, (2005)).

Unfortunately, typical concentrations required to achieve this antimicrobial activity impart a strong odor and flavor component that makes formulation difficult or impossible without conferring offensive organoleptic properties to the end product. (Oladunjoye, A. et al. Synergistic activity between lauric arginate and carvacrol in reducing *Salmonella* in ground turkey. *Poult. Sci.* 92:1357-1365 (2013). Bitar, A., Ghaddar, T., Malek, A., Haddad, T. & Toufeili, I. Sensory Thresholds of Selected Phenolic Constituents from Thyme and their Antioxidant Potential in Sunflower Oil. *J. Am. Oil Chem. Soc.* 85:641-64 (2008)). Maintaining the antimicrobial effect of the plant extract while reducing the concentration needed below or near the sensory threshold would result in a versatile and desirable product that is likely to be widely accepted by consumers. The usage of essential oils as a food preservative is limited due to the high flavor profile, which flavor profile negatively impacts the organoleptic property of the applied food.

Maintaining the antimicrobial effect of the plant extract while reducing the concentration needed below or near the sensory threshold would result in a versatile and desirable product that is likely to be widely accepted by consumers. One common approach to diminishing the concentration required of an antimicrobial while maintaining overall functionality is through the discovery and use of synergistic combinations of agents. Synergy refers to a combined effect that is greater than the sum of the effects observed by the agents when they are used in isolation.

Lauric arginate (LAE) is a cationic surfactant that has widely reported antimicrobial activity. (Oladunjoye, A. et al. Synergistic activity between lauric arginate and carvacrol in reducing *Salmonella* in ground turkey. *Poult. Sci.* 92:1357-1365 (2013). Soni, K. A., Desai, M., Oladunjoye. A., Skrobot, F. & Nannapaneni, R. Reduction of *Listeria monocytogenes* in queso fresco cheese by a combination of listericidal and listeriostatic GRAS antimicrobials. *Int. J. Food Microbial.* 155:82-88 (2012). Nair, D. V. T., Nannapaneni, R., Kiess, A., Mahmoud, B. & Sharma, C. S. Antimicrobial efficacy of lauric arginate against *Campylobacter jejuni* and spoilage organisms on chicken breast fillets. Poult. Sci. 93:2636-2640 (2014). Chang, Y., McLandsborough, L. & McClements, D. J. Fabrication, stability and efficacy of dual-component antimicrobial nanoemulsions: Essential oil (thyme oil) and cationic surfactant (lauric arginate). Food Chem. 172:298-304 (2015). DAI, Y., NORMAND, M. D., WEISS, J. & PELEG, M. Modeling the Efficacy of Triplet Antimicrobial Combinations: Yeast Suppression by Lauric Arginate, Cinnamic Acid, and Sodium Benzoate or Potassium Sorbate as a Case Study. J. Food Prot. 73:515-523 (2010)).

Lauric arginate is regarded as safe and acceptable for use as an antimicrobial agent in meat, dressings, and other applications. It has undergone toxicity testing and is rapidly digested in the human stomach to natural products. The manufacturer cites Generally Recognized As Safe (GRAS) regulatory status for lauric arginate (GRAS Notice No. GRN 000164) in a variety of products (including dressings, condiments, and soups) and at concentrations up to 200 ppm, as well as approved processing aid status in certain meat applications. Approvals—LAE. Available at: www.lauric-arginate.com (Accessed: 30 Nov. 2018).

One problem with LAE is that, as a cationic antimicrobial, its antimicrobial activity is reduced considerably when applied in complex food matrices due to binding with food components.

Previous work has examined lauric arginate in combination with several plant extracts (such as cinnamon leaf oil, thyme oil extracted from *Thymus vulgaris*, or carvacrol), however even after combining these extracts with lauric arginate the reported concentrations required to potentiate an antimicrobial effect are still well above the recorded taste thresholds, rendering them largely non-viable as antimicrobial products. (Ma, Q. Improving antimicrobial activity of lauric arginate by combination with essential oils for novel applications, PhD diss., University of Tennessee, 2015). Work to establish synergistic combinations has also not yielded promising results, with synergy only reported for cinnamon leaf oil and carvacrol, but at levels well above the sensory threshold (200 ppm for cinnamon leaf oil, and 60 ppm for carvacrol, a highly purified component of essential oils with less favorable labeling implications) (Oladunjoye, A. et al. Synergistic activity between lauric arginate and carvacrol in reducing *Salmonella* in ground turkey. *Poult Sci.* 92:1357-1365 (2013) and Ma, Q. Improving antimicrobial activity of lauric arginate by combination with essential oils for novel applications. PhD diss., University of Tennessee, 2015). Additionally, thymol (a potent antimicrobial found in thyme oil) was tested and determined not to possess synergy with lauric arginate. (Ma, Q., Davidson. P. M. & Zhong, Q. Antimicrobial properties of lauric arginate alone or in combination with essential oils in tryptic soy broth and 2% reduced fat milk. Int. J. Food Microbiol. 166:77-84 (2013)).

Delivery systems which maximize the bioavailability of essential oils are another potential strategy to increase their antimicrobial potential. Essential oils are slightly soluble in water, making long-term emulsification in an aqueous solution challenging as these solutions are highly susceptible to Ostwald ripening, hindering the ability of the oil to act as an antimicrobial. Use of a highly water-insoluble oil containing medium to long chain triglycerides (such as corn or canola oil) helps stabilize the essential oil by acting as a hydrophobic sink for the essential oil dispersion. (Chang, Y., McLandsborough, L. & McClements, D. J. Fabrication, stability and efficacy of dual-component antimicrobial nanoemulsions: Essential oil (thyme oil) and cationic surfactant (lauric arginate). Food Chem. 172:298-304 (2015)). Unfortunately, use of a carrier oil also seems to decrease the antimicrobial efficacy of the essential oil solution. (Chang, Y., McLandsborough, L. & McClements, D. J. Fabrication, stability and efficacy of dual-component antimicrobial nanoemulsions: Essential oil (thyme oil) and cationic surfactant (lauric arginate). Food Chem. 172:298-304 (2015)). Likely, some of the essential oil partitions into this hydrophobic sink instead of partitioning into microbial membranes and serving to disrupt essential cellular processes. Utilizing an ionic surfactant can help prevent Ostwald ripening by coating the essential oil droplets with a charged molecule, leading to repulsion between oil droplets and increased emulsion stability and essential oil availability. While previous work has successfully lowered the concentration of medium to long chain triglycerides containing oil required, even the lowest formulations still contain a significant portion, hindering the antimicrobial potential of the resulting emulsion. (Chang, Y., McLandsborough, L. & McClements, D. J. Fabrication, stability and efficacy of dual-component antimicrobial nanoemulsions: Essential oil (thyme oil) and cationic surfactant (lauric arginate). Food Chem. 172:298-304 (2015)). It is to be noted that these formulations include polysorbate 80, an emulsifier that is not naturally derived, and for which reported detrimental health effects could lead to negative perceptions of products and brands which utilize this emulsifier to incorporate essential oils into their formulations. (Singh, R. K. Wheildon, N. & Ishikawa, S. Food Additive P-80 Impacts Mouse Gut Microbiota Promoting Intestinal Inflammation, Obesity and Liver Dysfunction. *SOJ* Microbiol. Infect. Dis, Vol. 4, (2016). Chassaing, B. et al. Dietary emulsifiers impact the mouse gut microbiota promoting colitis and metabolic syndrome. Nature 519:92-96 (2015). Holder, M. K. et al. Dietary emulsifiers consumption alters anxiety-like and social-related behaviors in mice in a sex-dependent manner. *Sci. Rep.* 9:172 (2019)).

The present invention identifies synergistic combinations which could effectively suppress the growth of spoilage microorganisms or pathogens at lower concentrations and thereby diminish the associated flavor impact of the constituent antimicrobials. These synergistic combinations find application in meat and poultry, sauces and dressings, salads, hummus, seafood, cosmetics and/or nutritional supplements.

OBJECT OF THE INVENTION

It is an object of the present invention to provide synergistic combinations of agents comprising known "clean-label" antimicrobial substances as well as processes for stabilizing food substances against typical food borne spoilage microorganisms and/or pathogens. The present synergistic composition and process is designed to replace current synthetic antimicrobials and processes which utilize synthetic antimicrobials, such as sodium diacetate, potassium lactate, and sodium benzoate. It is a further object of the invention to provide synergistic combinations of "clean label" antimicrobials which may be employed in such a process, wherein the antimicrobial combinations of agents are utilized at levels below sensory thresholds, for example, in food substances and cosmetics.

SUMMARY OF THE INVENTION

The present invention relates to antimicrobial compositions comprising a plant essential oil extract and lauric arginate, wherein the composition is in the form of a stabile emulsion.

The invention contemplates such a composition, wherein the plant extract is selected from thyme oil, an essential oil (or major active such as thymol from an essential oil) selected from oregano oil, rosemary oil, cassia oil, cinnamon oil, sage oil, pimento oil, black pepper oil, allspice oil, coriander oil, clove oil, citrus oil, garlic oil, onion oil, ginger oil, spearmint oil, cranberry extract, hop acids, hop extract, hop oils, pomegranate extract, green tea extract, as well as an oleoresin such as rosemary and deflavorized rosemary.

In a further embodiment, the plant essential oil extract constituent is thyme essential oil.

In a further embodiment, the plant essential oil extract may be incorporated into a use environment in an antimicrobial amount, wherein flavor and/or odor of the plant essential oil and LAE is undetectable.

In a further embodiment, the composition comprises a clean-label emulsifier.

In a further embodiment, the composition comprises 1% or less of a non-clean-label emulsifier.

The invention contemplates such a composition, wherein the composition does not comprise an emulsifier.

In a further embodiment, the composition exhibits synergistic antimicrobial activity.

In a further embodiment, the composition exhibits synergistic antimicrobial activity, wherein the plant essential oil and the lauric acid arginate are present in the composition in a ratio of 3.5:1 plant essential oil to lauric acid arginate, respectively.

The invention further contemplates a stabilized food, beverage, cosmetic and/or nutritional supplement comprising the antimicrobial composition.

The invention further contemplates a method for stabilizing foods, beverages, cosmetics and/or nutritional supplements comprising incorporating an effective amount of the antimicrobial composition of the invention.

The invention also contemplates methods wherein the antimicrobial composition comprises thyme essential oil and lauric arginate.

The invention also contemplates methods wherein the antimicrobial composition exhibits synergistic antimicrobial activity.

BRIEF DESCRIPTION OF THE DRAWINGS

FIG. 3A: Cells are treated to 52.5 ppm Thyme and 15 ppm lauric arginate (LAE) emulsion; 52.5 ppm Thyme essential oil alone; or 15 ppm lauric arginate alone. The percent values at top indicate the percent inhibited, as compared to the growth control (no treatment). FIG. 3 B: Cells are treated to 38.5 ppm Thyme and 11 ppm lauric arginate (LAE) emulsion, 38.5 ppm Thyme essential oil alone; or 11 ppm lauric arginate alone. The percent values at top indicate the percent inhibited, as compared to the growth control (no treatment).

DETAILED DESCRIPTION OF THE INVENTION

Figure 1:
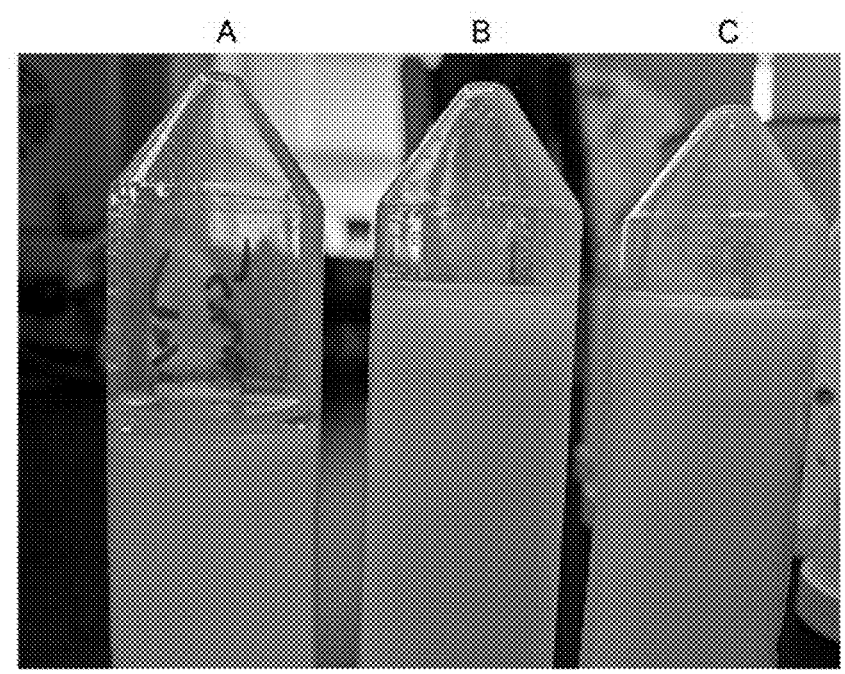
FIG. 1 shows emulsion stability testing of 10% oil-in-water emulsions containing within the oil phase, a 50:50 mixture of canola oil and thyme oil. A: no emulsifier control; B: emulsion containing 1% polysorbate 80; and C: 0.9% polysorbate 80 with 0.1% lauric arginate containing emulsion. Oil separating out is visible at the top of the tubes, with the no emulsifier control containing the most separated oil and the emulsion containing 0.1% lauric arginate with the least separated oil.

With the instant invention, the cationic surfactant lauric arginate is evaluated as a stabilizer/antimicrobial specifically to formulate an essential oil-based antimicrobial which may be effective against the industrially relevant and acid resistant spoilage yeast *Zygosaccharomyces bailii*. This organism is particularly problematic as it is resistant to acids and high osmotic stress, as well as capable of growth in oxygen depleted environments, representing resistance to typical processing and packaging technologies designed to prevent microbiologic growth. (Kuanyshev, N., Adamo, G. M., Porro, D. & Branduardi, P. The spoilage yeast *Zygosaccharomyces bailii*: Foe or friend? *Yeast* 34:359-370 (2017)). This extreme resistance and robustness in the face of antimicrobial countermeasures has resulted in a dearth of clean-label solutions to inhibit contamination and subsequent spoilage of food products by *Z. bailii*.

With the instant invention, a clean label antimicrobial solution to *Zygosaccharomyces bailii* has been identified which utilizes an essential oil based nanoemulsion in which the concentration of essential oil required in order to make product formulation possible has been significantly decreased. In addition, "clean label" formulations have been identified, which formulations represent a delivery system with both a quick kill step that constitutes a processing aid (given end use consistent with that definition) and longer acting antimicrobial suppression, to maximize the effect of the initial reduction in microbial population.

Emulsifiers as defined in the instant application as "clean label" emulsifiers may be selected from, for example, q-natural, gum arabic, hop acids, and hop fractions.

Emulsifiers as defined in the instant application as "non-clean-label" emulsifiers may be selected from, for example, polysorbate 80 and polysorbate 20, mono-glyceride, di-glyceride, DATEM (diacetyl tartaric acid esters of mono- and diglycerides) and modified starch are also considered non-clean label.

Aqueous phases contemplated under the instant invention include ethanol, water, maltodextrin, acidified water, buffer, propylene glycol, glycerin, or some other carrier.

The microstatic agents contemplated under the instant invention include, in addition to thyme oil, an essential oil (or major active such as thymol from an essential oil) selected from oregano oil, rosemary oil, cassia oil, cinnamon oil, sage oil, pimento oil, black pepper oil, allspice oil, coriander oil, clove oil, citrus oil, garlic oil, onion oil, ginger oil, spearmint oil, cranberry extract, hop acids, hop extract, hop oils, pomegranate extract, green tea extract, as well as an oleoresin such as rosemary, deflavorized rosemary, or other plant extract.

In an embodiment, the essential oil is thyme oil. The thyme oil comprises thymol as a major component. The thyme oil may be an extract of *Thymus zygis* Loefl, the extract produced according to methods utilized by those skilled in the art.

In some iterations, the emulsion is diluted into a final food product at levels such that the lauric arginate is present at concentrations ranging from 5-5000 ppm. The thyme oil (or other plant essential oil) is dosed such that the concentration in the final product is between 1-5000 ppm.

In some iterations, the emulsion is diluted into a final food product at levels such that the lauric arginate is present at concentrations ranging from about 0.2-60 ppm and the thyme essential oil is dosed such that the concentration in the final product is between about 1-200 ppm.

In an embodiment, the ratio of thyme essential oil to LAE is 3.5 ppm to 1 ppm, respectively, in the synergistic combinations of the invention.

EXAMPLES

Oil-in-water emulsions are prepared as follows: 10% oil-in-water emulsions containing within the oil phase, a 50:50 mixture of canola oil and thyme oil are combined with 1% polysorbate 80 or are combined with 0.9% polysorbate 80 with 0.1% lauric arginate; 7% oil-in-water emulsions containing 7% thyme oil and 2% lauric arginate or containing 7% thyme oil, 1% lauric arginate and 1% polysorbate 80 (including pH 4, 0.005M citrate buffer for the aqueous phase) were mixed at maximum speed for 2 minutes using a small lab scale blender. Emulsions are stored in inverted 50 ml conical tubes and assessed for stability by visually examining for oil separation.

In an embodiment, emulsions of the invention are prepared by combining 7% thyme oil and 2% lauric arginate (a 3.5:1 ratio, respectively); or by combining 7% thyme oil, 1% lauric arginate and 1% polysorbate 80.

Antimicrobial efficacy of emulsions of the invention is assessed by back diluting a mid-log phase, overnight culture of Z. bailii 1:100 into fresh acidified (pH 5) yeast peptone dextrose broth and adding the appropriate concentration of emulsion. Emulsions are prepared and tested in duplicate. Controls of lauric arginate are prepared in the same buffer with corn oil substituted for essential oil, at the same concentration. To test thyme oil alone, ethanol is used as a vehicle to solubilize the thyme oil in the microbiological media.

Antimicrobial efficacy of emulsions is assessed by back diluting a mid-log phase, overnight culture of an organism belonging to a subset of gram-negative bacteria, gram-positive bacteria, yeast, or mold, including but not limited to the following genera: Zygosaccharomyces, Lactobacillus, Pseudomonas, Escherichia, Acinetobacter, Campylobacter, Helicobacter, Bacillus, Salmonella, Listeria, Clostridium, Vibrio, Candida, Saccharomyces, Aspergillus, Geotrichum, Pichia, Phoma, Paecilomyces, Shewanella, Stachybotrys, Penicillium, Cladosporium, Rhizopus, Byssochlammys, Pediococcus, Leuconostoc, Oenococcus, Xanthomonas, Yersinia, Obesumbacterium, Proteus, Serratia, Psychrobacter, Brochothrix, Alcaligenes, Flavobacterium, Moraxella, Photobacterium, Phytophthora, Erwinia, Propionibacterium, Alicyclobacillus, Enterobacter, and Microbacterium. The overnight culture is diluted 1:100 into fresh microbiological broth and the appropriate concentration of emulsion is added.

Organoleptic characteristics of the emulsions of the invention are evaluated in studies in which 38.5 ppm thyme oil in marinara sauce (the lowest level used in this study to demonstrate synergy with lauric arginate) is given in a triangle test along with two undosed samples. Respondents are unable to detect the difference in samples in a statistically significant manner. The study is repeated, however instead of 38.5 ppm thyme oil, the marinara is dosed such that the final concentration of thyme oil is 200 ppm (the lowest dose demonstrated in the prior art to have antimicrobial effect). Respondents are able to detect a sensory difference between 200 ppm thyme oil and 38.5 thyme oil in marinara sauce in a statistically significant manner.

The lowest amount of Thyme oil which demonstrated an antimicrobial effect was above the sensory threshold. This is specifically important because the taste impact of thyme oil limits its application in food products.

Thus, the emulsions of the invention comprising combinations of thyme oil and LAE which demonstrate synergy when combined at a 3.5:1 ratio, respectively, may be utilized in food substances and cosmetics and surprisingly provide antimicrobial efficacy at concentrations below sensory thresholds.

Emulsions of Thyme Oil

In an embodiment, thyme oil was emulsified along with an Ostwalt ripening inhibitor (canola oil) using polysorbate 80, and lauric arginate. Canola oil and thyme oil were mixed in a 50:50 ratio and added such that the final emulsion contained 10% oil. Three types of emulsions were prepared: a control (containing only oil and buffer, no emulsifier), a 1% polysorbate 80 emulsion, and a 0.9% polysorbate 80 emulsion with 0.1% lauric arginate (see FIG. 1). Oil separating out from the emulsion is visible at the top of the tubes, with the control containing the most separated oil and the emulsion containing 0.1% lauric arginate with the least separated oil. Thus, the emulsion containing lauric arginate performed better, with less oil separation visible after the 2-week test period.

Figure 2:
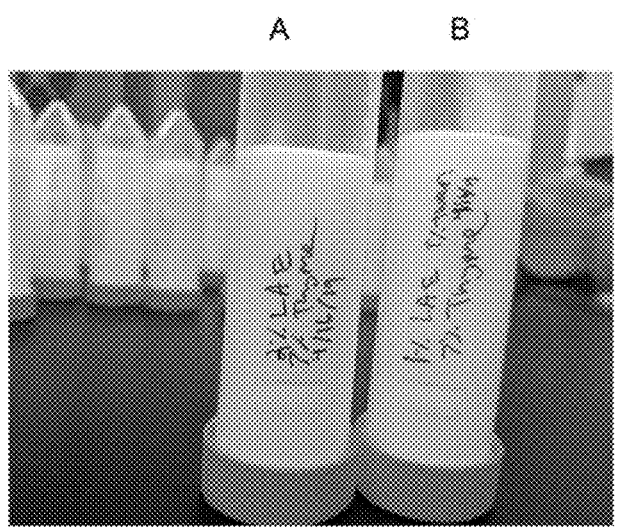
FIG. 2 shows emulsion stability testing of 7% oil-in-water emulsions comprising 7% thyme oil. A: 2% lauric arginate and 7% thyme oil; B: emulsion containing 7% thyme oil, 1% lauric arginate and 1% polysorbate 80. Image was captured after 24 hours. A very slight oil layer is visible at top of both, however, both emulsifying systems seem to perform equally well.

In order to create an optimally "clean" or "clean-label" formulation that maximizes the bioavailability of the thyme oil, formulations were prepared eliminating the Ostwalt ripening inhibitor and the polysorbate 80. 7% oil-in-water emulsions which comprise 7% thyme oil and 2% lauric arginate or comprise 7% thyme oil and 1% LAE and 1% polysorbate 80 were prepared and observed after 24 hours (FIG. 2). A very slight oil layer is visible at the top of both emulsions; however, both emulsifying systems perform equally well. Surprisingly, removing both the Ostwalt ripening inhibitor and the polysorbate 80 did not result in significant separation of the oil and water components.

Antimicrobial Activity of Emulsions

Figure 3:
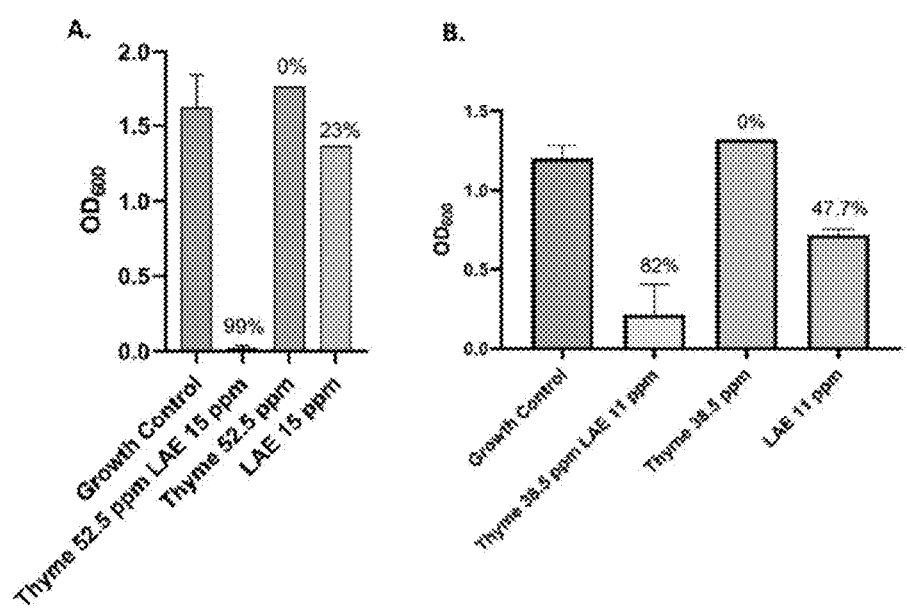
FIG. 3 shows antimicrobial testing of lauric arginate (LAE) and thyme emulsions evaluating growth of *Z. bailii* under differing conditions, as measured by optical density at 600 nm.

The antimicrobial efficacy of the formulations was evaluated against the relevant spoilage organism Z. bailii after 72 hours of incubation, as measured by optical density at 600 nm. See FIG. 3 which compares the growth of Z. bailii under differing conditions. Z. bailii was treated to emulsions comprising 52.5 ppm Thyme oil and 15 ppm lauric arginate (LAE); 52.5 ppm Thyme essential oil alone; or 15 ppm lauric arginate alone. The percent values at the top of the bars in FIG. 3 indicate the percent Z. bailii inhibited, as compared to the growth control (no treatment).

Despite the lack of synergy detected between thymol and lauric arginate in previous studies, unexpected synergy was observed in the compositions of the present invention (FIG. 3A). The synergy was also observed at even lower concentrations of thyme and lauric arginate, with a lower boundary of 38.5 ppm thyme oil and 11 ppm lauric arginate (FIG. 3B).

These data represent a significant improvement over the understanding in the art, which identified 200 ppm thyme oil as the lower boundary exhibiting antimicrobial activity against Z. bailii, and only in a formulation requiring the addition of polysorbate 80 and corn oil.

Thus, it is unexpected that antimicrobial activity is demonstrated at a concentration less than ⅕ of that which had been previously reported for thyme oil alone and, moreover, that this activity is observed in the absence of both the polysorbate 80 and the Ostwalt ripening inhibitor.

The emulsion compositions of the invention comprising synergistic amounts of thyme oil and LAE, which emulsions do not require polysorbate 80 and an Ostwalt ripening inhibitor, provide an advantage for use in food products for the fact that the food products may be packaged under a "clean-label" designation, conferring a significant product advantage and being widely accepted by consumers.

Figure 4:
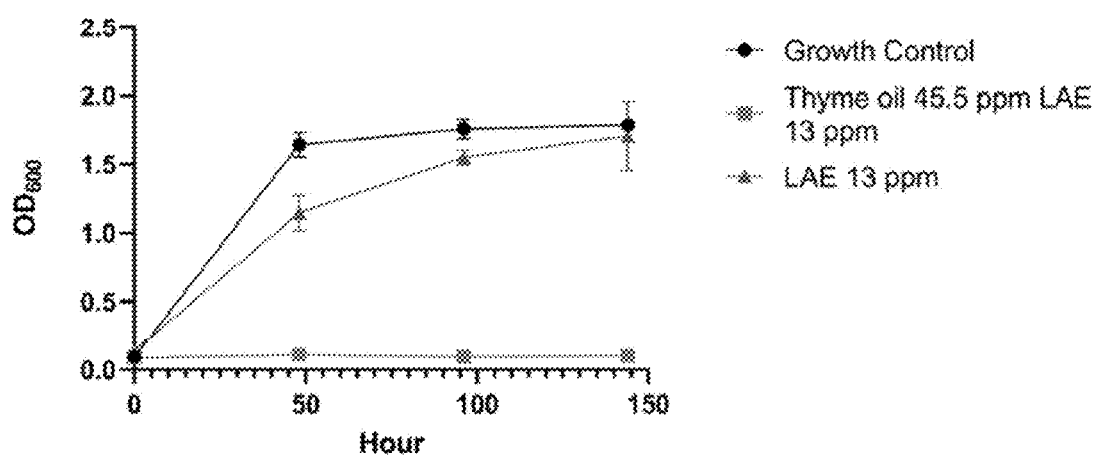
FIG. 4 shows temporal analysis of emulsion performance evaluating growth of *Z. bailii* under differing conditions over time, as measured by optical density at 600 nm. Growth control (circles), Thyme oil and lauric arginate (LAE) emulsion treated (squares), lauric arginate (LAE) alone (triangles).

Additional studies were conducted in order to ascertain the temporal component of lauric arginate activity. As many regulatory bodies do not require the addition of processing aids to the final label, a formulation in which the lauric arginate functions in a manner consistent with a processing aid could confer a significant product advantage. Time-course studies with the inventive emulsions were performed. Cells are treated to 45.5 ppm Thyme oil and 13 ppm lauric arginate (LAE) emulsion; 45.5 ppm Thyme essential oil alone; or 13 ppm lauric arginate alone, and the $OD_{600}$ of the cultures were measured over time. FIG. 4. Shows growth of Z. bailii treated to emulsion comprising 45.5 ppm thyme oil and 13 ppm LAE (a 3.5:1 ratio of thyme oil to LAE, respectively); lauric arginate alone, or growth control (no lauric arginate) as measured by optical density at 600 nm.

Interestingly, the concentration of lauric arginate that was inhibitory when present in an emulsion with thyme was not inhibitory when emulsified without thyme, with the yeast growing to the exact same optical density as the control culture. These data suggest that lauric arginate is serving a short-term role in the emulsion with a longer lasting effect potentiated by the thyme oil. Product formulations incorporating this antimicrobial emulsion may then only be required to list the thyme oil on their label, a significant product advantage over multi-ingredient formulations.

The instant invention identifies and evaluates antimicrobial synergy of an emulsion comprising essential oil thyme and the cationic surfactant lauric arginate. The demonstrated synergy exists at concentrations markedly different when compared to prior art studies (at 38.5 ppm thyme compared to previous work testing as low as 200 ppm), and in novel formulations comprising a 3.5:1 ratio of thyme oil to LAE, respectively, which represent a significant improvement in "clean-label" status of the resulting antimicrobial concentrate (by removing polysorbate 80 and the Ostwalt ripening inhibitor, previously thought to be essential components of the antimicrobial formulation). This is particularly surprising given that prior work had tested for synergy between the major antimicrobial component of thyme oil (thymol) and found no synergy to be present. Additionally, the resulting antimicrobial formulation may be considered "clean-label" given that the data indicates lauric arginate potentiates a quick kill-step (qualifying as a processing aid which would not appear on the label), while the essential oil serves to maintain the decrease in microbial population over the long term (and would thus warrant inclusion on the final label).

The emulsion compositions and methods of the invention utilize a specific ratio (3.5:1) of thyme oil and LAE, respectively, which emulsion compositions demonstrate markedly improved synergy. Utilizing the compositions/combinations of the invention having the ratio of 3.5:1 thyme oil to LAE, the compositions of the invention may be added to the use environment in antimicrobial amounts, for example at 38.5 ppm thyme oil, which is below the sensory threshold.

Specific embodiments disclosed herein may be further limited in the claims using "consisting of" or "consisting essentially of language". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s).

As used herein, the term "comprising" or "comprises" is intended to mean that the compositions and methods include the recited elements, but not excluding others.

As used herein, the terms "optional" or "optionally" mean that the subsequently described event or condition may need not occur, and that the description includes instances where the event or condition occurs and instances in which it does not.

The term "effective amount" refers to that quantity of a compound or combination composition that is sufficient to result in antimicrobial activity.

An effective amount of a synergistic composition comprising or consisting essentially of a plant essential oil extract, lauric arginate and, optionally, an emulsifier, for example thyme essential oil and LAE, results in antimicrobial activity in the use environment, wherein flavor and/or odor of the plant essential oil and LAE is below the sensory threshold.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. An antimicrobial composition comprising thyme essential oil and lauric arginate (LAE), wherein the thyme essential oil and the lauric acid arginate are present in the composition in a ratio of 3.5:1 thyme essential oil to lauric acid arginate, respectively, and wherein the composition is in the form of a stabile emulsion,
   wherein the antimicrobial composition is incorporated into a food, beverage, cosmetic and/or nutritional supplement in an amount in which the thyme essential oil is less than 200 ppm in the food, beverage, cosmetic and/or nutritional supplement.

2. The antimicrobial composition of claim 1, wherein the thyme essential oil may be incorporated into a use environment in an antimicrobial amount, wherein flavor and/or odor of the thyme essential oil and LAE is undetectable.

3. The antimicrobial composition of claim 1, wherein the composition comprises less than 1% emulsifier.

4. The antimicrobial composition of claim 1, wherein the composition exhibits synergistic antimicrobial activity.

5. A stabilized food, beverage, cosmetic and/or nutritional supplement comprising the antimicrobial composition of claim 1.

6. A method for stabilizing foods, beverages, cosmetics and/or nutritional supplements comprising incorporating an effective amount of the antimicrobial composition of claim 1.

7. The method of claim 6, wherein the composition exhibits synergistic antimicrobial activity.

8. The method of claim 6, wherein the thyme essential oil is incorporated into foods, beverages, cosmetics and/or nutritional supplements in an antimicrobial amount, wherein flavor and/or odor of the thyme essential oil and LAE is undetectable.

* * * * *